United States Patent [19]

Brown et al.

[11] Patent Number: 4,988,695

[45] Date of Patent: Jan. 29, 1991

[54] PYRROLOCINNOLINES FOR USE AS INHIBITORS OF GASTRIC ACID SECRETION

[75] Inventors: Thomas H. Brown, Tewin; Peter Blurton, Welwyn Garden City, both of England

[73] Assignee: Smith Kline & French Laboratories Limited, Welwyn Garden City, United Kingdom

[21] Appl. No.: 468,523

[22] Filed: Jan. 23, 1990

[30] Foreign Application Priority Data

Jan. 23, 1989 [GB] United Kingdom ............. 8901430.2

[51] Int. Cl.$^5$ .................... C07D 487/04; A61K 31/50
[52] U.S. Cl. .................................. 514/248; 544/234; 544/235; 564/442
[58] Field of Search ....................... 544/234; 514/248

[56] References Cited

PUBLICATIONS

Cirrincione et al., *Chemical Abstracts,* vol. 105, No. 133852 (1986).
Dattolo et al., *Chemical Abstracts,* vol. 97, No. 23744 (1982).
Jan, *Chemical Abstracts,* vol. 94, No. 22884 (1981).

*Primary Examiner*—Mukund J. Shah
*Assistant Examiner*—E. Bernhardt
*Attorney, Agent, or Firm*—Linda E. Hall; Stuart R. Suter; Edward T. Lentz

[57] ABSTRACT

Pyrrolo- and dihydropyrrolocinnolines, and their use as inhibitors of gastric acid secretion. A compound of the invention is 1-(2-methylphenyl)-2,3-dihydropyrrolo-[3,2-c]-cinnoline.

14 Claims, No Drawings

PYRROLOCINNOLINES FOR USE AS INHIBITORS OF GASTRIC ACID SECRETION

The present invention relates to substituted cinnoline derivatives, processes for their preparation, intermediates useful in their preparation, pharmaceutical compositions containing them and their use in therapy.

Accordingly the present invention provides, in a first aspect compounds of structure (I)

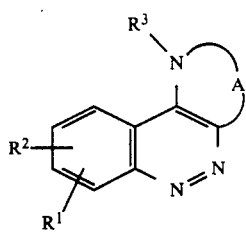

in which
R$^1$ and R$^2$ are the same or different and are each hydrogen, C$_{1-6}$alkyl, C$_{1-6}$alkoxy, phenyl, C$_{1-6}$alkylthio, C$_{1-6}$alkanoyl, amino, C$_{1-6}$alkylamino, diC$_{1-6}$alkylamino, halogen or trifluoromethyl;
R$^3$ is hydrogen, C$_{1-6}$alkyl or a group

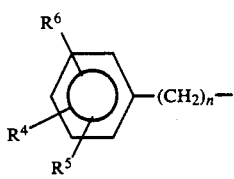

R$^4$ to R$^6$ are the same or different and are each hydrogen, C$_{1-6}$alkyl, C$_{1-6}$alkoxy, C$_{1-6}$alkylthio, halogen, cyano, amino, hydroxy, carbamoyl, carboxy, C$_{1-6}$alkanoyl or trifluoromethyl;
n is 0 to 4; and
A is —(CH$_2$)$_2$—, —(CH$_2$)$_3$— or —CH=CH—;
or a salt thereof.

Suitably, R$^1$ and R$^2$ are the same or different and are each, hydrogen, C$_{1-6}$alkyl, C$_{1-6}$alkoxy, phenyl, C$_{1-6}$alkylthio, C$_{1-6}$alkanoyl, amino, C$_{1-6}$alkylamino, diC$_{1-6}$alkylamino, halogen or trifluoromethyl. Preferably, one of R$^1$ and R$^2$ is hydrogen and the other is hydrogen or C$_{1-6}$alkyl.

Suitably, R$^3$ is hydrogen, C$_{1-6}$alkyl or

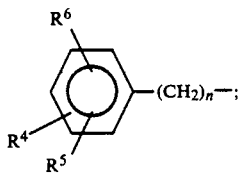

Preferably, R$^3$ is C$_{1-6}$alkyl or

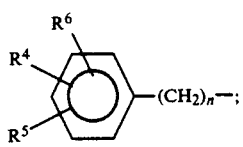

Suitably R$^4$ to R$^6$ are the same or different and are each hydrogen, C$_{1-6}$alkyl, C$_{1-6}$alkoxy, C$_{1-6}$alkylthio, halogen, cyano, amino, hydroxy, carbamoyl, carboxy, C$_{1-6}$alkanoyl or trifluoromethyl. Preferably one of R$^4$ to R$^6$ is hydrogen and the other two are the same or different and are hydrogen, C$_{1-6}$alkyl or hydroxy.

Suitably n is 0 to 4; preferably n is 0.
Suitably A is —(CH$_2$)$_3$—, —(CH$_2$)$_2$ or CH=CH; preferably A is —(CH$_2$)$_2$—.

C$_{1-6}$alkyl groups (either alone or as part of another group) can be straight or branched.

It will be appreciated that compounds of structure (I) in which one or more of R$^1$ to R$^6$ is a C$_{3-6}$alkyl group (either alone or as part of another group) may contain an assymetric centre due to the presence of the C$_{3-6}$alkyl group. Such compounds will exist as optical isomers (enantiomers). Both the pure enantiomers, racemic mixtures (50% of each enantiomer) and unequal mixtures of the two are included within the scope of the present invention. Further, all diastereomeric forms possible (pure enantiomers and mixtures thereof) are within the scope of the invention.

The present invention provides in a further aspect a process for the preparation of a compound of structure (I) or a pharmaceutically acceptable salt thereof which comprises cyclisation of a compound of structure (II)

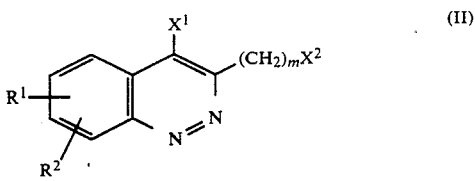

in which R$^1$ and R$^2$ are as described for structure (I); m is 2 or 3 and X$^1$ and X$^2$ are leaving groups, in the presence of a compound of structure R$^3$NH$_2$ or R$^3$NH$_3$+Cl$^-$ (III) in which R$^3$ is as described for structure (I); or
oxidising a compound in which A is (CH$_2$)$_2$ to a compound in which A is —CH=CH—;
forming a salt.

Suitable leaving groups X$^1$ and X$^2$ will be apparent to those skilled in the art and include for example halogen, in particular chlorine.

Suitably the cyclisation of a compound of structure (II) in the presence of a compound of structure (III) is carried out in a solvent and at a temperature of between ambient and the reflux temperature of the solvent used. Preferably the reaction is carried out at elevated temperature in a suitable solvent. For example, in a solvent such as I,4-Dioxan or phenol at elevated temperature. Suitably the compound (III) is present as the free base, preferably in the protonated form R$^3$NH$_3$⊕Cl⊖.

Suitable reagents for carrying out the oxidation of compounds of structure (I) in which A is (CH$_2$)$_2$ to compounds of structure (I) in which A is CH=CH will be apparent to those skilled in the art and include, for example, dehydrogenation in the presence of a noble metal catalyst, in particular palladium-on-carbon. Under certain conditions, as described in the examples hereinafter, the dehydrogenation can also take place in the absence of a solid catalyst.

Acid addition salts of the compounds of structure (I) in particular pharmaceutically acceptable salts can be prepared by standard procedures by, for example, reaction with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as, for example, citric, maleic or fumaric acids.

The intermediate compounds of structure (II) are new and as such form a further aspect of the present invention. They can be prepared by procedures analogous to those known in the art. For example, compounds of structure (II) in which both $X^1$ and $X^2$ are chloro can be prepared by the reaction sequence outlined in Scheme 1.

Scheme I

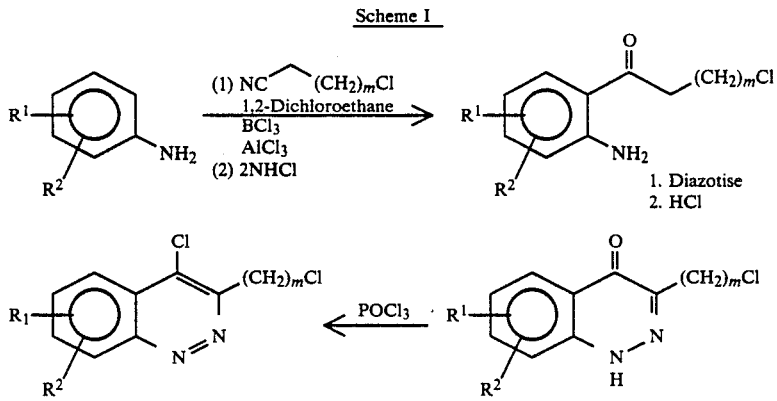

It is to be noted, and apparent to those skilled in the art that in the foregoing reactions, where necessary, groups $R^1$ to $R^6$ will be in protected form when undergoing the procedures described.

The compounds of structure (I) and their pharmaceutically acceptable salts and related compounds for which no pharmaceutical utility has been previously disclosed exert an anti-secretory effect by inhibition of the gastrointestinal $H^+K^+ATPase$ enzyme (Fellenius E., Berglindh T., Sachs G., Olke L., Elander B., Sjostrand S.E., and Wahlmark B., 1981, Nature, 290, 159–61).

In a further aspect therefore the present invention provides a method of inhibiting exogenously and endogenously stimulated gastric acid secretion which comprises administering to a subject in need thereof an effective amount of a compound of structure (I) or a pharmaceutically acceptable salt thereof. In addition the present invention provides a method of treatment of gastrointestinal diseases in mammals, in particular humans, which comprises administering to a subject in need thereof, an effective amount of a compound of structure (I) or a pharmaceutically acceptable salt thereof. Such diseases include, for example, gastric and duodenal ulcers, and Zollinger-Ellison Syndrome.

Further, in another aspect of the invention the compounds of structure (I) can be used in the treatment of other disorders where an anti-secretory effect is desirable for example in patients with gastritis, NSAID induced gastritis, gastric ulcers, acute upper intestinal bleeding, in patients with a history of chronic and excessive alcohol consumption, and in patients with gastro oesophageal reflux disease (GERD).

In the methods of the invention, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of structure (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of structure (I) or a pharmaceutically acceptable salt thereof calculated as the free base.

The pharmaceutically acceptable compounds of the invention will normally be administered to a subject for the treatment of gastro-intestinal diseases and other conditions caused or exacerbated by gastric acidity. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of structure (I) or a pharmaceutically acceptable salt thereof calculated as the free base, the compound being administered 1 to 4 times per day. Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-flammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16,16 dimethyl $PGE_2$, or histamine $H_2$-antagonists (for example, cimetidine).

The following examples illustrate the invention. Temperatures are recorded in degrees centigrade.

Example 1

1-(2-Methylphenyl)-2,3-dihydropyrrolo[3,2-c]cinnoline (a) 1-(2-Aminophenyl)-4-chlorobutan-1-one hydrochloride To a solution of boron trichloride (55 g) in 1,2-dichloroethane (200 ml) at 0° was added dropwise a solution of aniline (39.1 g, 0.42 mol) in 1,2-dichloroethane (50 ml) maintaining the temperature below 5°. On completion of the addition 4-chlorobutyronitrile (41.4 g, 0.42 mol) and aluminium chloride (53.34 g, 0.42 mol) were added successively and the reaction mixture allowed to warm up to room temperature then heated under reflux for 20 hours. After allowing to cool, 2N hydrochloric acid (100 ml) was added and the reaction mixture heated under reflux for 0.5 hour. The solid obtained was collected by filtration, taken up in water and extracted with chloroform (5×200 ml). The chloroform extracts were combined, washed with dilute base, then water, dried over magnesium sulphate, filtered and evaporated under reduced pressure to give an oil. The oil was dissolved in ether and ethanolic HCl was added, the resulting solid was collected by filtration and dried, 28.5 g. Recrystallization from ethanol/diethyl ether gave the product, m.p. 152–154°

$C_{10}H_{12}ClNO$ HCl,
Found C 5.27, H 5.52, N 6.02, Cl 15.11, Cl⁻ 15.10%;
Requires C 51.30, H 5.60, N 5.98, Cl 15.15, Cl⁻ 15.15%.

(b) 3-(2-Chloroethyl)-4-oxo-(1H)-cinnoline.

A solution of 1-(2-aminophenyl)-4-chlorobutan-1-one hydrochloride (b 11.3 g, 0.0427 mol) in concentrated hydrochloric acid (1200 ml) was cooled down to 0° with stirring. Then sodium nitrite (3.54 g, 0.051mol) in water (25 ml) was added dropwise. On completion of the addition, the reaction mixture was allowed to warm to room temperature and stirred overnight. The solution was evaporated under reduced pressure to dryness. The solid obtained was washed with a solution of sodium acetate and collected by filtration to give the title compound, 5.32 g. Recrystallization from methanol gave the product, m.p. 201–203°.

$C_{10}H_9ClN_2O$
Found C 57.53, H 4.23, N 13.28, Cl 16.84%;
Requires C 57.56, H 4.35, N 13.43, Cl 16.99%.

(c) 3-(2-Chloroethyl)-4-chlorocinnoline.

3-(2-Chloroethyl)-4-oxo-(1H)-cinnoline (9 g, 0.043 mol) and phosphorus oxychloride (90 ml) were heated under reflux for 1 hour. After allowing to cool, the excess phosphorus oxychloride was evaporated under reduced pressure and the residue was poured onto ice (100 g), basified with concentrated ammonia solution, and extracted with chloroform (3×100 ml). The chloroform extracts were combined, dried over magnesium sulphate and evaporated under reduced pressure to give a solid, 8.00 g. Recrystallization from diethyl ether gave the title compound, m.p. 81–82°.

$C_{10}H_8Cl_2N_2$
Found C 52.98, H 3.68, N 12.21, Cl 30.82%;
Requires C 52.89, H 3.55, N 12.34, Cl 31.23%.

(d) 1-(2-Methylphenyl)-2,3-dihydropyrrolo[3,2-c]cinnoline.

4-Chloro-3-(2-chloroethyl)cinnoline (1.52 g, 0.0067 mol) and o-toluidine (1.43 g, 0.0134 mol) in 1,4 dioxan (20 ml) were heated under reflux for 20 hours. The solvent was evaporated under reduced pressure and the residue was partitioned between chloroform and dilute sodium bicarbonate solution. The aqueous layer was extracted with chloroform (6×50 ml). The chloroform extracts were combined, dried over magnesium sulphate, filtered and evaporated under reduced pressure to give a brown oil. The oil was purified by chromatography using chloroform (1 litre), chloroform/methanol (20:1) as eluant. The fractions containing the product were combined and evaporated under reduced pressure to give an oil. On trituration with diethyl ether a solid was obtained. The solid was collected by filtration and dried, 0.76 g. Recrystallization from ethyl acetate gave the title compound, 0.48 g, m.p. 140–142°.

$C_{17}H_{15}N_3$,
Found C 77.71, H 5.81, N 16.01%;
Requires C 78.13, H 5.78, N 16.08%.

EXAMPLE 2

1-(2-methylphenyl)-6-methyl-2,3-dihydropyrrolo[3,2-c]cinnoline (a) 1-(2-Amino-3-methylphenyl)-4-chlorobutan-1-one hydrochloride.

To a solution of boron trichloride (55 g) in 1,2 dichloroethane at 0° was added dropwise a solution of o-toluidine (45.7 g, 0.426 mol) in 1,2 dichloroethane (50 ml) maintaining the temperature below 5°. On completion of the addition 4-chlorobutyronitrile (41.4 g, 0.426 mol) and aluminium chloride (53.34 g, 0.426 mol) were added successively. The reaction mixture was allowed to warm up to room temperature and stirred for 1.5 hours, then heated under reflux for 20 hours. The reaction mixture was then cooled to room temperature poured onto ice (500 g) and 2N hydrochloric acid (200 ml). The mixture was then heated under reflux for 0.5 hour. The organic layer was separated and the aqueous layer was extracted with chloroform (3×100 ml). The organic extracts were combined, washed with water, dried over magnesium sulphate, filtered and evaporated under reduced pressure to give an oil. The oil was dissolved in diethyl ether and HCl gas bubbled through. The resulting solid was collected by filtration and dried (57 g). Recrystallization from ethanol/diethyl ether gave the title compound, m.p. 148-150°.

C$_{11}$H$_{14}$ClNO HCl,
Found C 53.25, H 6.03, N 5.64, Cl 14.09, Cl$^-$ 14.19%
Requires C 53.24 H 6.09, N 5.64, Cl 14.19, Cl$^-$ 14.19%.

(b) 3-(2-Chloroethyl)-8-methyl-4-oxo-(1H)-cinnoline.

To a solution of 1-(2-amino-3-methylphenyl)-4-chlorobutan-1-one hydrochloride (20 g, 0.081 Mol) and concentrated hydrochloric acid (1000 ml) at 0° was added dropwise a solution of sodium nitrite (6.07 g, 0.088 mol) in water (50 ml) maintaining the temperature below 5°. The reaction mixture was stirred at room temperature for 20 hours. The solvent was evaporated under reduced pressure to give a solid. The solid was washed with sodium acetate solution and collected by filtration and dried, 13.5 g. Recrystallization from methanol gave the title compound, m.p. 222-225°

C$_{11}$H$_{11}$ClN$_2$O
Found C 59.27, H 4.98, N 12.50, Cl 15.04%;
Requires C 59.33, H 4.98, N 12.58, Cl 14.98%.

(c) 3-(2-Chloroethyl)-4-chloro-8-methylcinnoline.

3-(2-Chloroethyl)-8-methyl-4-oxo-(1H)-cinnoline (9 g, 0.04 mol) and phosphorus oxychloride (100 ml) were heated under reflux for 2 hours. The excess phosphorus oxychloride was evaporated under reduced pressure and the residue was poured onto ice, basified with concentrated ammonia solution and extracted with chloroform (3×200 ml). The chloroform extracts were combined, dried over magnesium sulphate, filtered and evaporated under reduced pressure to give a dark brown solid. Recrystallization from diethyl ether/petroleum ether (b.p. 40-60°) gave an analytically pure sample, m.p. 102-104°

C$_{11}$H$_{10}$Cl$_2$N$_2$,
Found C 55.12, H 4.09, N 11.78, Cl 29.41%;
Requires C 54.79, H 4.18, N 11.62, Cl 29.41%.

(d) 1-(2-Methylphenyl)-6-methyl-2,3-dihydropyrrolo[3,2-c]-cinnoline.

3-(2-Chloroethyl)-4-chloro-8-methylcinnoline (2.5 g, 0.01mol) and o-toluidine hydrochloride (1.4 g, 0.01 mol) in 1,4 dioxan (20 ml) were heated under reflux for 20 hours. The solvent was evaporated under reduced pressure to give an oil. The oil was partitioned between chloroform and dilute sodium carbonate solution and extracted further with chloroform (4×100 ml). The chloroform extracts were combined, dried over magnesium sulphate, filtered and evaporated to give an oil. The oil was purified by column chromatography using dichloromethane then chloroform as eluant. The solid obtained was recrystallized from diethyl ether/ dichloromethane to give the title compound, 0.6 g, m.p. 135-137°.

C$_{18}$H$_{17}$N$_3$,
Found C 78.49, H 6.31, N 15.30%;
Requires C 78.52, H 6.22, N 15.26%.

EXAMPLE 3

1-(2-Methylphenyl)-6-methylpyrrolo[3,2-c]cinnoline.

To a refluxing slurry of 10% Pd/C (0.4 g) in diphenyl ether (20 ml) was added 1-(2-methylphenyl)-6-methyl-2,3-dihydropyrrolo [3,2-c]cinnoline (1.25 g, 0.0045 mol). After 0.5 hour at reflux temperature the reaction mixture was cooled, diluted with chloroform and the catalyst was filtered off over hyflo. The product was isolated by column chromatography using dichloromethane (11) then chloroform. The oil obtained was crystallized from ethyl acetate, 0.42 g, m.p. 105-106°.

C$_{18}$H$_{15}$N$_3$,
Found C 79.10, H 5.61, N 15.48%;
Requires C 79.09, H 5.53, N 15.37%.

EXAMPLE 4

1-(4-Hydroxy-2-methylphenyl)-2,3-dihydropyrrolo[3,2-c]-cinnoline hydrochloride

4-Chloro-3-(2-chloroethyl)cinnoline (1 g, 0.0044 mol) and 4-hydroxy-2-methylphenylamine (0.54 g, 0.0044 mol) in 1,4 dioxan (20 ml) were heated under reflux for 20 hours. The solid obtained was collected by filtration and dried. Recrystallization from ethanol gave the title compound, 0.4 g, m.p. >300°

C$_{17}$H$_{15}$N$_3$O HCl
Found C 64.67, H 5.18, N 13.14, Cl$^-$ 11.16%;
Requires C 65.07, H 5.14, N 13.39, Cl$^-$ 11.30%.

EXAMPLE 5

N-propyl-2,3-dihydropyrrolo[3,2-c]cinnoline 3-(2-Chloroethyl)-4-chlorocinnoline (2 g, 0.088 mol), propylamine (4 g, 0.067 mol) and phenol (2 g, 0.0212 mol) were heated in an oil bath at 160° for 20 hours. The reaction mixture was diluted with chloroform (200 ml) and extracted with 2N sodium hydroxide (3×100 ml). The chloroform extracts were then washed with water (50 ml), dried over magnesium sulphate, filtered and evaporated under reduced pressure to give an oil. The oil was purified by chromatography using a gradient elution chloroform/methanol (0-5% MeOH). The fractions containing the product were combined and evaporated to give a yellow solid, 1.4 g. Recrystallization from ethyl acetate gave the title compound, 1.21 g, m.p. 116-118°.

C$_{13}$H$_{15}$N$_3$,
Found C 73.20, H 7.10, N 19.72%;
Requires C 73.21, H 7.09, N 19.70%.

EXAMPLE 6

N-Benzylpyrrolo[3,2-c]cinnoline 3-(2-Chloroethyl)-4-chlorocinnoline (2 g, 0.0088 mol), benzylamine (4 g, 0.037 mol) and phenol (2 g, 0.0212 mol) were heated in an oil bath at 160° for 20 hours. The reaction had not gone to completion so the temperature was raised to 190° for a further 6 hours. The reaction mixture was dissolved in chloroform (300 ml) and extracted with 2N sodium hydroxide (3×100 ml). The chloroform extracts were washed with water (100 ml), dried over magnesium sulphate, filtered and evaporated under reduced pressure to give an oil. The oil was purified by chromatography using chloroform as eluant. The fractions containing the product were combined and evaporated to dryness to give a brown solid. Recrystallization from isopropyl alcohol gave the title compound, 0.5 g, m.p. 190-192°.

C$_{17}$H$_{13}$N$_3$,
Found C 78.72, H 5.02, N 16.01%;
Requires C 78.74, H 5.05, N 16.21%.

EXAMPLE 7

1-(4-Hydroxy-2-methylphenyl)-6-methyl-2,3-dihydropyrrolo-[3,2-c]cinnoline hydrochloride.

3-(2-Chloroethyl)-4-chloro-8-methylcinnoline (2 g, 0.0083 mol) and 4-hydroxy-2-methylaniline hydrochloride (1.32 g, 0.0083 mol) in isopropanol (50 ml) were heated under reflux in a nitrogen atmosphere for 20 hours. The solid obtained was collected by filtration and dried. Recrystallization from isopropanol/ethanolic HCl gave the title compound as a partial hydrate, 0.64 g, m.p. 292-294°.

$C_{18}H_{17}N_3O$ HCl 0.6$H_2O$
Found C 63.69, H 5.73, N 12.39, Cl− 10.63%;
Requires C 63.84, H 5.71, N 12.40, Cl− 10.47%.

EXAMPLE A

A tablet for oral administration is prepared by combining

|  | Mg/Tablet |
| --- | --- |
| Compound of structure (I) | 100 |
| Mannitol | 153 |
| Starch | 33 |
| crospovidone | 12 |
| microcrystalline cellulose | 30 |
| magnesium stearate | 2 |
|  | 330 mg | into a 9 mm tablet.

EXAMPLE B

An injection for parenteral administration was prepared from the following

| Compound of Structure 1 | 6.68% (w:v) |
| --- | --- |
| 1M citric acid | 30% (v:v) |
| sodium hydroxide (qs) to | pH 3.2 |
| water for injection EP to | 100 ml |

The compound of Structure 1 was dissolved in the citric acid and the pH slowly adjusted to pH 3.2 with the sodium hydroxide solution. The solution was then made up to 100 ml with water, sterilised by filtration and sealed into appropriately sized ampoules and vials.

Biological Data.

(A) $H^+K^+$ATPase Activity.

The effects of a single high concentration (100 μM) of a compound of structure (I) on $K^+$-stimulated ATPase activity in lyophilised gastric vesicles was determined. Preferred compounds of structure (I) were also tested over a range of concentrations to determine $IC_{50}$ values.

(i) Preparation of hilised gastric vesicles (H/K-ATPase).

Lyophilised gastric vesicles were prepared from pig fundic mucosa after the method of Keeling et. al. (Biochem. Pharmacol., 34, 2967, 1985).

(ii) $K^+$-stimulated ATPase activity.

$K^+$-stimulated ATPase activity was determined at 37° in the presence of the following: 10 mM Pipes/Tris buffer pH 7.0, 2 mM $MgSO_4$, 1 mM KCl, 2 mM $Na_2ATP$ and 3 μg protein/ml lyophilised gastric vesicles. After incubation for 30 minutes, the inorganic phosphate hydrolysed from ATP was determined by the method of Yoda and Hokin (Biochem. Biophys. Res. Commun. 40, 880, 1970).

Compounds of structure (I) were dissolved in dimethylsulphoxide which up to the highest concentration used had no effect on $K^+$-stimulated ATPase activity.

The effect of the highest concentration of each compound of structure (I) on the recovery of a standard amount of inorganic phosphate was also determined.

(iii) Results.

The compounds of each of examples 1 to 5 were assayed in the above-noted screen and found to have $IC_{50}$ values in the range of from 1.8 to 11.1 μM.

What is claimed is:

1. A compound of structure (I)

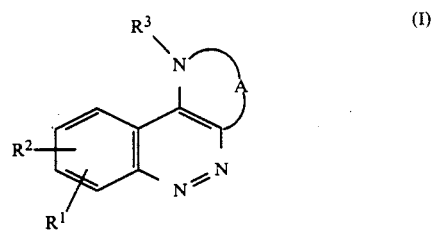

in which
R¹ and R² are the same or different and are each hydrogen, $C_{1-6}$alkyl, $C_{1-6}$alkoxy, phenyl, $C_{1-6}$alkylthio, $C_{1-6}$alkanoyl, amino, $C_{1-6}$alkylamino, diCl$_{1-6}$alkylamino, halogen or trifluoromethyl;
R³ is hydrogen, $C_{1-6}$ or a group

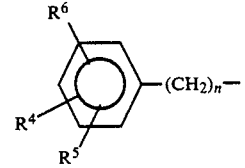

R⁴ to R⁶ are the same or different and are each hydrogen, $C_{1-6}$alkyl, $C_{1-6}$alkoxy, $C_{1-6}$alkylthio, halogen, cyano, amino, hydroxy, carbamoyl, carboxy, $C_{1-6}$alkanoyl or trifluoromethyl;
n is 0 to 4; and
A is —(CH₂)₂—, —(CH₂)₃— or —CH=CH—; or a pharmaceutically acceptable salt thereof.

2. A compound according to claim 1 in which A is —(CH₂)₂—.

3. A compound according to claim 1 in which R³ is $C_{1-6}$alkyl or

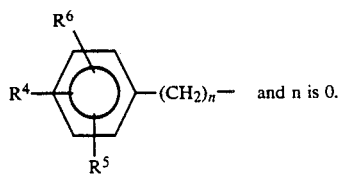

and n is 0.

4. A compound according to claim 3 in which one of R⁴ to R⁶ is hydrogen and the other two are the same or different and are hydrogen, $R_{1-6}$alkyl or hydroxy.

5. A compound according to claim 1 which is 1-(2-methylphenyl)-2,3-dihydropyrrolo[3,2-c]cinnoline.

6. A compound according to claim 1 which is 1-(2-methylphenyl)-6-methyl-2,3-dihydropyrrolo[3,2-c]cinnoline.

7. A compound according to claim 1 which is 1-(2-methylphenyl)-6-methylpyrrolo[3,2-c]cinnoline.

8. A compound according to claim 1 which is 1-(4-hydroxy-2-methylphenyl)-2,3-dihydropyrrolo[3,2-c]cinnoline hydrochloride.

9. A compound according to claim 1 which is N-propyl-2,3-dihydropyrrolo[3,2-c]cinnoline.

10. A compound according to claim 1 which is N-Benzylpyrrolo[3,2-c]cinnoline.

11. A compound according to claim 1 which is 1-(4-Hydroxy-2-methylphenyl)-6-methyl-2,3-dihydropyrrolo[3,2-c]cinnoline hydrochloride.

12. A pharmaceutical composition for the inhibition of gastric acid secretion comprising a compound of structure (I) as described in claim 1, or a pharmaceutically acceptable salt thereof and a pharmaceutical carrier.

13. A method of inhibiting exogenously and endogenously stimulated gastric acid secretion in mammals, which comprises administering to a subject in need thereof an effective amount of a compound of structure (I) or a pharmaceutically acceptable salt thereof as described in claim (I).

14. A method of treatment of gastrointestinal diseases in mammals which comprises administering to a subject in need thereof an effective amount of a compound of structure (I) or a pharmaceutically acceptable salt thereof as described in claim (I).

* * * * *